United States Patent [19]
Giraudon

[11] 3,985,782
[45] Oct. 12, 1976

[54] PHENYLTHIOUREA DERIVATIVES
[75] Inventor: Raymond Giraudon, Lesigny, France
[73] Assignee: Rhone-Poulenc S.A., Paris, France
[22] Filed: May 13, 1971
[21] Appl. No.: 143,216

[30] Foreign Application Priority Data
May 15, 1970  France .............................. 70.17838

[52] U.S. Cl. ............................. 260/455 A; 424/300
[51] Int. Cl.² ................ C07C 155/02; C07C 155/08
[58] Field of Search .................... 260/455 A, 552 R; 424/300, 322

[56] References Cited
UNITED STATES PATENTS

| | | | |
|---|---|---|---|
| 2,711,421 | 6/1955 | Mull. | 260/455 A |
| 2,943,972 | 7/1960 | Van der Kerk | 424/300 |
| 3,455,948 | 7/1968 | Stedman | 260/552 R |
| 3,470,232 | 9/1969 | Duennenberger et al. | 424/300 |
| 3,609,177 | 9/1971 | Traber et al. | 424/300 |

FOREIGN PATENTS OR APPLICATIONS

| | | | |
|---|---|---|---|
| 722,080 | 3/1969 | Belgium | 260/455 A |
| 8,262 | 3/1968 | Japan | 260/455 A |
| 16,980 | 7/1968 | Japan | 260/455 A |
| 6,909,225 | 12/1969 | Netherlands | 260/455 A |

Primary Examiner—Glennon H. Hollrah
Attorney, Agent, or Firm—Stevens, Davis, Miller & Mosher

[57] ABSTRACT

Compounds of the formula:

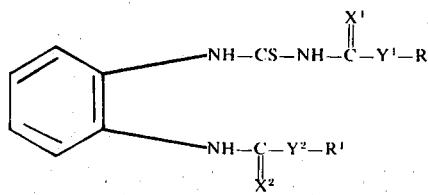

wherein R and $R^1$ represent alkyl of 1 through 4 carbon atoms, $X^1$ and $Y^1$ represent oxygen or sulphur, and $X^2$ and $Y^2$ represent oxygen or sulphur, at least one of $X^2$ and $Y^2$ representing sulphur, possess fungicidal and anthelmintic properties.

15 Claims, No Drawings

PHENYLTHIOUREA DERIVATIVES

This invention relates to new phenylthiourea derivatives, to processes for their preparation and to compositions containing them.

The phenylthiourea derivatives of the present invention are those of the general formula:

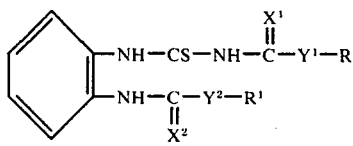

wherein R and $R^1$ are the same or different, and each represents an alkyl group of 1 to 4 carbon atoms (preferably a methyl, ethyl or propyl group), $X^1$ and $Y^1$ are the same or different and each represents an oxygen or sulphur atom, and $X^2$ and $Y^2$ are the same or different and each represents an oxygen or sulphur atom, at least one of $X^2$ and $Y^2$ representing a sulphur atom. Preferably $X^1$ and $Y^1$ represent oxygen atoms and $X^2$ represents a sulphur atom.

According to a feature of the invention, the phenylthiourea derivatives of general formula I are prepared by reacting a compound of the general formula:

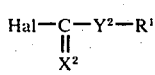

(wherein Hal represents a halogen atom, preferably a chlorine atom, and $X^2$, $Y^2$ and $R^1$ are as hereinbefore defined) with an o-phenylenediamine derivative of the general formula:

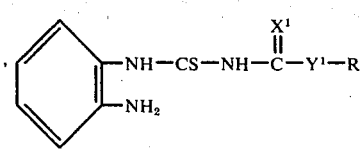

wherein $X^1$, $Y^1$ and R are as hereinbefore defined. The reaction is preferably carried out in an organic basic solvent, such as pyridine, at a temperature between 20° and 100° C. It is possible, however, to perform the reaction in a very polar solvent, such as dimethylformamide or dimethylsulphoxide, in the presence of a base such as triethylamine or dimethylaniline.

According to another feature of the invention, the phenylthiourea derivatives of general formula I are prepared by reacting an isothiocyanate of the general formula:

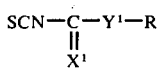

(wherein $X^1$, $Y^1$ and R are as hereinbefore defined) with an o-phenylenediamine derivative of the general formula:

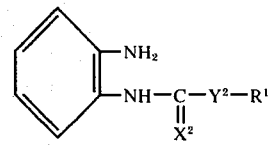

wherein $X^2$, $Y^2$ and $R^1$ are as hereinbefore defined. The reaction is generally effected in an inert organic solvent, such as acetone or benzene, at a temperature between 0° and 50° C.

According to a still further feature of the invention, the phenylthiourea derivatives of general formula I are prepared by reacting a compound of the general formula:

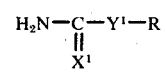

(wherein $X^1$, $Y^1$ and R are as hereinbefore defined), or an alkali metal (e.g., sodium) derivative thereof, with an isothiocyanate of the general formula:

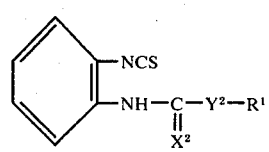

wherein the various symbols are as hereinbefore defined. The reaction may be carried out in an inert organic solvent such as benzene at a temperature between 0° C. and the boiling point of the reaction mixture. Preferably an alkali metal derivative of the compound of general formula VI is used and may be prepared by reaction of a compound of general formula VI with, for example, sodium hydride.

The o-phenylenediamine derivatives of general formula III can be obtained by reaction of o-phenylenediamine with one equivalent of an isothiocyanate of general formula IV, which may be prepared in situ.

The isothiocyanates of general formula IV can be prepared by reaction of a compound of the general formula:

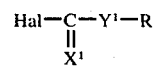

(wherein the various symbols are as hereinbefore defined) with an alkali metal thiocyanate.

The o-phenylenediamine derivatives of general formula V can be prepared by reacting a compound of general formula II with o-nitroaniline, followed by reduction of the nitro group in the resulting product to an amino group by methods known per se for the reduction of a nitro to an amino group.

When $X^2$ and $Y^2$ both represent sulphur atoms, the o-phenylenediamine derivatives of general formula V can be obtained by the action of a reactive ester of the general formula $Z-R^1$ (wherein $R^1$ is as hereinbefore defined and Z represents the residue of a reactive ester, e.g., a halogen atom) with ammonium (2-aminophenyl)dithiocarbamate.

The isothiocyanates of general formula VII can be obtained by the action of thiophosgene on o-phenylenediamine derivatives of general formula V.

The phenylthioureas of general formula I possess useful fungicidal properties; they have particularly interesting contact action against cucumber mildew (*Erysiphe cichoracearum*), apple mildew (*Podosphaera leucotricha*), bean anthracnose (*Colletotrichum lindemuthianum*) and wheat rust (*Puccinia glumarum*) when applied at quantities of between 10 and 50 g. per hectoliter of liquid diluent. They furthermore have the advantage of being systemic, in particular when they are applied by sprinkling soil with liquid compositions containing them, against bean anthracnose and against cucumber mildew, at doses greater than or equal to 0.1 g./hectoliter. The preferred compounds as fungicides are of general formula I, wherein R and $R^1$ are the same or different and each represents a methyl, ethyl or propyl group, $X^1$ and $Y^1$ represent oxygen atoms, $X^2$ represents a sulphur atom and $Y^2$ represents an oxygen or sulphur atom. Particularly preferred compounds are 1-[2-(ethoxythiocarbonylamino)phenyl]-3-methoxycarbonylthiourea, 1-[2-(propylthiothiocarbonylamino)phenyl]-3-methoxycarbonylthiourea, and 1-[2-(methoxythiocarbonylamino)phenyl]-3-methoxycarbonylthiourea.

The phenylthioureas of general formula I also possess useful anthelmintic properties. In vitro, they have shown themselves particularly active against the larvae of digestive threadworms of horses at concentrations between 1 g. and 1 mg. per liter of solution. In vivo, they have shown themselves active against *Haemonchus contortus*, *Trichostrongylus axei* and *Trichostrongylus colubriformis* at doses of 15 mg./kg. animal body weight when administered orally to sheep.

The preferred compounds as anthelmintics are of general formula I, wherein R and $R^1$ are the same or different and each represents a methyl or ethyl group, $X^1$ and $Y^1$ represent oxygen atoms, $X^2$ represents a sulphur atom and $Y^2$ represents an oxygen or sulphur atom. Particularly preferred compounds are 1-[2-(ethoxythiocarbonylamino)phenyl]-3-methoxycarbonylthiourea, 1-[2-(ethoxythiocarbonylamino)phenyl]-3-ethoxycarbonylthiourea and 1-[2-(methylthiothiocarbonylamino)phenyl]-3-methoxycarbonylthiourea.

The following Examples illustrate the preparation of phenylthioureas of the present invention. Melting points of the compounds were determined on a Kofler bench.

EXAMPLE 1

Ethyl chlorothionocarbonate (9.3 g.) is added over 4 minutes to a solution of 2-(3-methoxycarbonylthioureido)aniline (15.7 g.) in anhydrous pyridine (100 cc.). The temperature of the reaction medium rises from 22° to 39° C. Thereafter the mixture is left for 3 hours at a temperature of about 20° C. The reaction mixture is then poured into water (1 liter) and the oil, which separates out, is extracted with methylene chloride (2 × 200 cc.). The combined organic layers are washed successively with water (200 cc.), 3N hydrochloric acid (2 × 300 cc.) and water (200 cc.). The organic layer is dried, treated with decolorizing charcoal and filtered, and the filtrate is evaporated under reduced pressure. The crystalline residue (20 g.), (m.p. about 160° C.) is recrystallised from ethanol to produce 1-[2-(ethoxythiocarbonylamino)phenyl]-3-methoxycarbonylthiourea (9.3 g.), m.p. 172° C.

2-(3-Methoxycarbonylthioureido)aniline (43.5 g.), m.p. 177° C, can be prepared by reaction of o-phenylenediamine (52 g.) with the reaction product of methyl chloroformate (47 g.) with potassium thiocyanate (50 g.) in acetone (250 cc.) at a temperature of about −10° C.

Ethyl chlorothionocarbonate (b.p. 63°–68° C./60 mm.Hg.) can be prepared according to the process described by D. Martin and W. Mucke, Ber. 98, 2059 (1965).

EXAMPLE 2

1-[2-(Ethoxythiocarbonylamino)phenyl]-3-ethoxycarbonylthiourea (6.5 g.), m.p. 166° C, is prepared following the procedure of Example 1, substituting 2-(3-ethoxycarbonylthioureido)aniline (12 g.) for 2-(3-methoxycarbonylthioureido)aniline.

EXAMPLE 3

Methyl chloroformate (11.3 g.) is added to a solution of potassium thiocyanate (12.1 g.) in acetone (150 cc.) over 2 minutes with stirring, followed by heating of the mixture to 40° C for ½ hour. The resulting suspension is then cooled to 5° C and methyl 2-aminophenyldithiocarbamate (15.8 g.) is added in one portion. The mixture is cooled externally to control the initial exothermic reaction, and is then stirred for 15 hours at a temperature of about 20° C. Thereafter the reaction mixture is diluted with water (200 cc.) to precipitate crystals, which are filtered off, and successively washed with water (2 × 50 cc.), ethanol (2 × 20 cc.) and petroleum ether (b.p. 60°–80° C; 2 × 40 cc.). After drying under reduced pressure, 1-[2-(methylthiothiocarbonylamino)phenyl]-3-methoxycarbonylthiourea (19 g.), melting at 166° C., is obtained.

The methyl 2-aminophenyl-dithiocarbamate used as the starting material can be prepared as follows:

Methyl iodide (99.4 g.) is added to a solution of ammonium 2-aminophenyl-dithiocarbamate (141 g.) in water (1050 cc.), whilst keeping the temperature at about 20° C. The mixture is stirred for a further hour after the end of the exothermic reaction. The precipitate obtained is filtered off and is then recrystallized moist from ethanol. Methyl 2-aminophenyl-dithiocarbamate (125 g.), m.p. 114° C., is thus obtained.

Ammonium (2-aminophenyl)dithiocarbamate, m.p. about 140° C, can be prepared according to Lusanitch, Ber. 40, 2973 (1907).

In a similar manner but starting with methyl chloroformate and appropriate compounds of formula V, the following compounds are prepared: 1-[2-(ethylthiothiocarbonylamino)phenyl]-3-methoxycarbonylthiourea, m.p. 128° C; and 1-[2-(propylthiothiocarbonylamino)phenyl]-3-methoxycarbonylthiourea, m.p. 100° C.

EXAMPLE 4

The products listed below are prepared following the procedure described in Example 3, using appropriate starting materials of general formulae IV and V: 1-[2-(methoxythiocarbonylamino)phenyl]-3-methoxycarbonylthiourea, m.p. 162° C. (dec.); 1-[2-(methylthiothiocarbonylamino)phenyl]-3-n-propoxycarbonylthiourea, m.p. 142° C; 1-[2-(methylthio-carbonylamino)phenyl]-3-methoxycarbonylthiourea, m.p. 190° C; and 1-[2-(methylthiothiocarbonylamino)phenyl]-3-(methylthio)carbonylthiourea, m.p. 163° C.

According to a further feature of the present invention, there are provided fungicidal compositions which contain, as the active ingredient, at least one phenylthiourea derivative of general formula I in association with one or more diluents or adjuvants compatible with the phenylthiourea derivative(s) and suitable for use in agricultural fungicidal compositions. These compositions can optionally contain other compatible pesticides, such as insecticides or antimildew agents (e.g., maneb). Preferably the compositions contain between 0.005 and 80% by weight of phenylthiourea derivative.

The compositions may be solid if there is employed a powdered solid compatible diluent such as talc, calcined magnesia, kieselguhr, tricalcium phosphate, powdered cork, adsorbent charcoal, or a clay such as kaolin or bentonite. These solid compositions are preferably prepared by grinding the phenylthiourea derivative with the solid diluent, or by impregnating the solid diluent with a solution of the phenylthiourea derivative in a volatile solvent, evaporating the solvent, and if necessary grinding the product so as to obtain a powder.

Instead of a solid diluent, there may be used a liquid in which the phenylthiourea derivative is dissolved or dispersed. The compositions may thus take the form of suspensions, emulsions or solutions in organic or aqueous-organic media, for example aromatic hydrocarbons such as toluene or xylene, mineral, animal or vegetable oils, or acetophenone, or mistures of these diluents. The compositions in the form of suspensions, emulsions or solutions may contain wetting, dispersing or emulsifying agents of the ionic or non-ionic type, for example sulphoricinoleates, quaternary ammonium derivatives or products based on condensates of ethylene oxide, such as the condensates of ethylene oxide with octylphenol, or fatty acid esters of anhydrosorbitols which have been rendered soluble by etherification of the free hydroxyl groups by condensation with ethylene oxide. It is preferable to use agents of the non-ionic type because they are not sensitive to electrolytes. When emulsions are required, the phenylthiourea derivatives may be used in the form of self-emulsifying concentrates containing the active substance dissolved in the emulsifying agent or in a solvent containing an emulsifying agent compatible with the phenylthiourea derivative and solvent, a simple addition of water to such concentrates producing compositions ready for use.

The phenylthiourea derivatives of general formula I when used as fungicides are preferably employed in quantities of 5 to 200 g. per hectoliter of, for example, water.

The following Example illustrates fungicidal compositions of the present invention.

EXAMPLE 5

A condensation product (10 parts) of octylphenol and ethylene oxide in the ratio of 10 moles of ethylene oxide per mole of octylphenol is added to a solution of 1-[2-(ethoxythiocarbonylamino)phenyl]-3-methoxycarbonylthiourea (25 parts) in a mixture (65 parts) of equal parts of toluene and of acetophenone, the said parts being parts by weight.

The solution obtained is used after dilution with water in the ratio of 100 cc. of solution per 100 liters of water to protect plants against attacks by fungi.

The present invention also includes pharmaceutical and veterinary compositions which comprise, as the active ingredient, at least one phenylthiourea derivative of general formula I in association with a carrier or coating generally used in the preparation of pharmaceutical and veterinary compositions. The compositions are preferably in a form suitable for oral administration.

Tablets, pills, powders or granules can be used as solid compositions for oral administration. In these compositions the phenylthiourea derivative is mixed with one or more inert diluents, such as sucrose, lactose or starch. These compositions can also contain substances other than diluents, for example lubricants such as magnesium stearate.

Pharmaceutically acceptable emulsions, solutions, suspensions, syrups and elixirs, containing inert diluents such as water or paraffin oil, can be used as liquid compositions for oral administration. These compositions can also contain substances other than the diluents, such as, for example, wetting agents or sweetening or flavoring agents.

In veterinary therapy, the phenylthiourea derivatives can be used for the treatment of nematodal helminthiases of cattle, sheep, goats and domestic animals in general, at single dosages of between 25 and 100 mg./kg. animal body weight, administered orally.

In human therapy, the phenylthiourea derivatives can be used at single dosages of between 10 and 50 mg./kg. administered orally. These dosages can be repeated at regular intervals of several days or several weeks to achieve definitive removal of the parasite.

In general, the physician or veterinary surgeon will decide the posology which is considered most appropriate, depending on the species in question as well as the age, the weight, the degree of infection and all other factors peculiar to the subject to be treated.

The following Example illustrates therapeutic compositions according to the invention.

EXAMPLE 6

Tablets, weighing 0.7 g., having the following composition are prepared in accordance with the usual technique:

| | |
|---|---|
| 1-[2-(methylthiothiocarbonylamino)phenyl]-3-methoxycarbonylthiourea | 0.500 g. |
| wheat starch | 0.150 g. |
| colloidal silica | 0.040 g. |
| magnesium stearate | 0.010 g. |

I claim:
1. Phenylthiourea derivatives of the general formula:

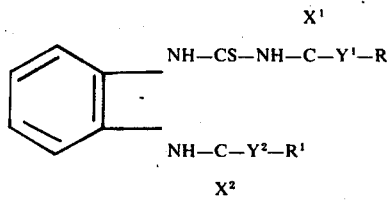

wherein R and $R^1$ represent alkyl of 1 through 4 carbon atoms, $X^1$ and $Y^1$ represent oxygen or sulphur, and $X^2$ and $Y^2$ represent oxygen or sulphur, at least one of $X^2$ and $Y^2$ representing sulphur.

2. Phenylthiourea derivatives according to claim 1 wherein $X^1$ and $Y^1$ both represent oxygen.

3. Phenylthiourea derivatives according to claim 1 wherein $X^2$ represents sulphur.

4. Phenylthiourea derivatives according to claim 1 wherein $Y^2$ represents sulphur.

5. Phenylthiourea derivatives according to claim 1 wherein R and $R^1$ represent methyl, ethyl or propyl, $X^1$ and $Y^1$ represent oxygen, $X^2$ represents sulphur and $Y^2$ represents oxygen or sulphur.

6. Phenylthiourea derivatives according to claim 1 wherein R and $R^1$ represent methyl or ethyl, $X^1$ and $Y^1$ represent oxygen, $X^2$ represents sulphur and $Y^2$ represents oxygen or sulphur.

7. The phenylthiourea derivative according to claim 1 which is 1-[2-(ethoxythiocarbonylamino)phenyl]-3-methoxycarbonylthiourea.

8. The phenylthiourea derivative according to claim 1 which is 1-[2-(ethoxythiocarbonylamino)phenyl]-3-ethoxycarbonylthiourea.

9. The phenylthiourea derivative according to claim 1 which is 1-[2-(methylthiothiocarbonylamino)phenyl]-3-methoxycarbonylthiourea.

10. The phenylthiourea derivative according to claim 1 which is 1-[2-(ethylthiothiocarbonylamino)phenyl]-3-methoxycarbonylthiourea.

11. The phenylthiourea derivative according to claim 1 which is 1-[2-(propylthiothiocarbonylamino)phenyl]-3-methoxycarbonylthiourea.

12. The phenylthiourea derivative according to claim 1 which is 1-[2-(methoxythiocarbonylamino)phenyl]-3-methoxycarbonylthiourea.

13. The phenylthiourea derivative according to claim 1 which is 1-[2-(methylthiothiocarbonylamino)phenyl]-3-propoxycarbonylthiourea.

14. The phenylthiourea derivative according to claim 1 which is 1-[2-(methylthio-carbonylamino)phenyl]-3-methoxycarbonylthiourea.

15. The phenylthiourea derivative according to claim 1 which is 1-[2-(methylthiothiocarbonylamino)phenyl]-3-(methylthio)carbonylthiourea.

* * * * *